United States Patent [19]

Dickey

[11] Patent Number: 4,726,903

[45] Date of Patent: * Feb. 23, 1988

[54] CONTINUOUS FLOW SEPARATION OR MIXING BY ELECTROPHORESIS WITH MOVING BOUNDARY SORPTION

[76] Inventor: Leland C. Dickey, 12335 Seward St., Omaha, Nebr. 68154

[ * ] Notice: The portion of the term of this patent subsequent to Oct. 22, 2002 has been disclaimed.

[21] Appl. No.: 853,440

[22] Filed: Apr. 18, 1986

Related U.S. Application Data

[63] Continuation-in-part of Ser. No. 752,097, Jul. 5, 1985, Pat. No. 4,599,225, which is a continuation-in-part of Ser. No. 638,255, Aug. 6, 1984, Pat. No. 4,548,802, which is a continuation-in-part of Ser. No. 561,899, Dec. 15, 1983, abandoned.

[51] Int. Cl.$^4$ .............................................. B01D 15/08
[52] U.S. Cl. ..................... 210/635; 210/656; 210/676; 210/748; 55/67; 55/77; 55/181; 55/386; 204/180.1; 204/299 R; 423/210; 423/659; 435/70; 435/174; 435/183; 435/184; 435/287; 435/803
[58] Field of Search .................. 204/180.1, 299 R; 55/34, 67, 77–79, 99, 181, 386, 390, 2; 423/219, 242 A, 659, 210; 210/656–659, 660, 670, 671, 676, 748; 422/70; 435/70, 174, 183, 184, 287, 83

[56] References Cited

U.S. PATENT DOCUMENTS

| | | | |
|---|---|---|---|
| 2,639,000 | 5/1953 | Edwards | 55/181 |
| 3,335,081 | 8/1967 | El-Naggar | 210/150 |
| 3,498,026 | 3/1970 | Messinger | 204/308 |
| 3,598,726 | 8/1971 | Welch | 210/151 |
| 3,757,492 | 9/1973 | Graff | 55/181 |
| 3,798,784 | 3/1974 | Kovats | 210/748 |
| 3,846,300 | 11/1974 | Inoue | 210/748 |
| 3,907,967 | 9/1975 | Filss | 423/210 |
| 3,962,069 | 6/1976 | Inoue | 210/748 |
| 4,100,068 | 7/1978 | Jordan | 55/2 |
| 4,101,400 | 7/1978 | Peppins | 210/748 |
| 4,242,107 | 12/1980 | Jenkins | 55/18 |
| 4,292,054 | 9/1981 | Noack | 55/181 |
| 4,351,650 | 9/1982 | Shinoda | 55/181 |
| 4,353,720 | 10/1982 | Margraf | 55/262 |
| 4,440,638 | 4/1984 | Judy | 210/748 |
| 4,454,016 | 6/1984 | Rabinowitz | 204/308 |
| 4,548,802 | 10/1985 | Dickey | 210/198.2 |
| 4,548,803 | 10/1985 | Dickey | 210/198.2 |
| 4,599,225 | 7/1986 | Dickey | 210/198.2 |

OTHER PUBLICATIONS

Perry's Chemical Engineers' Handbook, McGraw Hill, Fourth Edition, 1969, pp. 16-20, 16-24, and 16-25.

*Primary Examiner*—Ernest G. Therkorn
*Attorney, Agent, or Firm*—Zarley, McKee, Thomte, Voorhees & Sease

[57] ABSTRACT

A continuous process for separating charged components of a fluid mixture is disclosed which comprises forming a sorption zone and a desorption zone, said sorption and desorption zones being separated by a boundary of a sorbent material which continuously moves back and forth between the sorption and desorption zones, causing a fluid mixture to flow into the sorption zone wherein an electrical potential is imposed to promote sorption of one of the charged components of the mixture by the sorbent material, and imposing an electrical potential in the desorption zone such that the sorbed component will be desorbed when the sorbent material containing the sorbed component moves into the desorption zone. This sorption separation process may be used in a network (including a linear series) of sorption/desorption units for separation of multiple components of fluid mixture or for more complete separation of one component of a fluid mixture.

15 Claims, 4 Drawing Figures

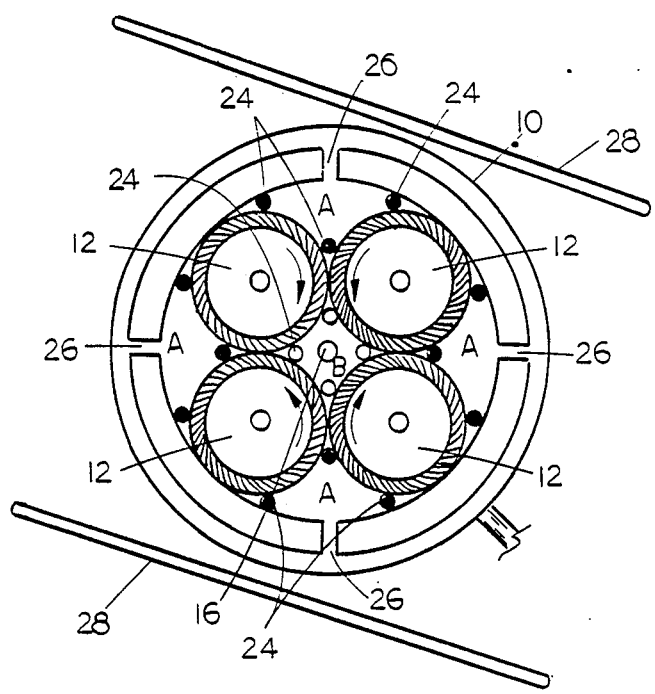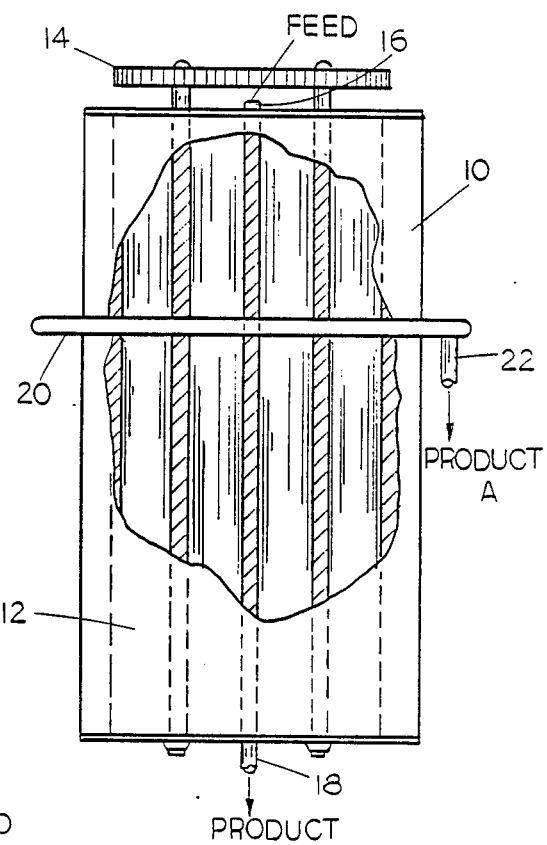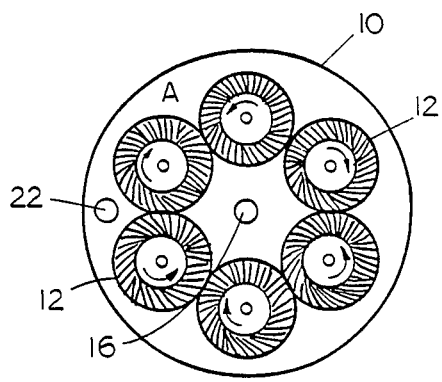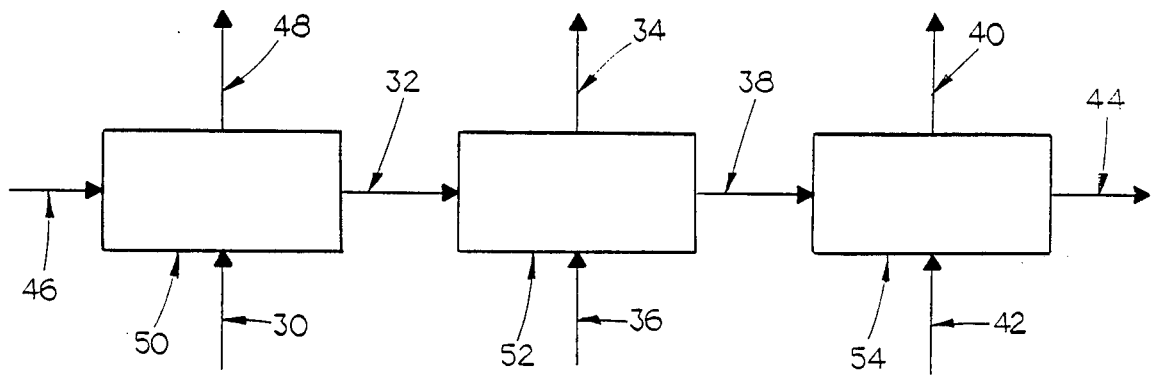

CONTINUOUS FLOW SEPARATION OR MIXING BY ELECTROPHORESIS WITH MOVING BOUNDARY SORPTION

REFERENCE TO RELATED APPLICATION

This application is a continuation-in-part of the application entitled "Continuous Flow Separation or Mixing with Moving Boundary Sorption", Ser. No. 752,097, filed July 5, 1985 now U.S. Pat. No. 4,599,225 which was a continuation-in-part of the application entitled "Continuous Flow Separation or Mixing with Moving Boundary Sorption", Ser. No. 638,255, filed Aug. 6, 1984 (now U.S. Pat. No. 4,548,802); which was a continuation-in-part of the application entitled "Continuous Flow Separation or Mixing with Moving Boundary Sorption", Ser. No. 561,899, filed Dec. 15, 1983, now abandoned.

BACKGROUND OF THE INVENTION

This invention relates to a continuous process for obtaining optimal separation of a fluid mixture by electrophoresis. The method also relates to a process for preparing precise fluid mixtures where the metered component is mixed by electrophoresis.

In recent years, cyclic separation processes have received considerable attention. Such processes as pressure-swing adsorption, parametric pumping, and cycling zone adsorption, separate continuous or semi-continuous fluid feed streams by cycling a thermodynamic variable which affects the mass transfer of fluid components with a sorption media. The cycle is designed to alternatively sorb and desorb components so the fluid components are separated and the media returns to its initial condition after the completion of a cycle. The feed and product streams can be rendered continuous by combining sorption units in parallel but each unit necessarily experiences discontinuous flow conditions so that the sorbing media can be altered by changing thermodynamic variables such as temperatures, pH, or pressure, for example, and so that the other product stream can be created thereby. The discontinuity of flow through or past the sorbing media creates inefficiency in the separations because of the mixing of fluid elements that have been exposed to the sorbing media under different conditions.

All practical separation techniques that occur with discontinuous flow result in product reservoir mixing. Since the feed mixture flows through the vessel during the sorption cycle of the cycling process, the sorbent will fill with the sorbed fluid component and the sorptivity will decrease. Thus, fluid entering the vessel early in the cycle is stripped of the sorbable constitutents to a greater extent than fluid entering late in the cycle. As a result, the composition of the fluid emerging from the sorbent zone is continually changing. Such a system cannot be controlled as efficiently as a single condition, continuous, time invariant process because in the cyclic operation you must compromise between optimizing for the early portion of the sorption cycle and the later portion. The ideal situation where product flow streams are not mixed would require a prohibitively large numbmer of separate reservoirs as well as a complicated flow management system.

It is an object of the present invention to provide a method for continuous flow separation or mixing which avoids the inefficiencies inherent in reservoir mixing. It is an object of the present invention to provide a method for continuous flow separation or mixing wherein a significant part of the seal between the sorption and desorption zones is the sorption media itself. Still another object of this invention is to provide an electrophoretic method for continuous flow separation.

SUMMARY OF THE INVENTION

The present invention relates to a continuous process for separating charged components of a fluid mixture which comprises first forming a sorption zone and a desorption zone. The two zones are separated by a boundary of a sorbent material which continuously moves back and forth between the zones. A fluid mixture is caused to flow into the sorption zone wherein the conditions are such to promote preferential sorption of at least one of the charged components of the mixture by the sorbent material. Finally, conditions are created in the desorption zone such that at least one of the sorbed components will be desorbed when the sorbent material containing it moves into the desorption zone.

An electrical potential is imposed in the sorption zone or the desorption zone or both to cause sorption and/or desorption of at least one of the charged components. The product from at least one of the zones may then be conveyed to another separator wherein the preceding steps are repeated. These steps can be repeated in as many other separators as are desired.

BRIEF DESCRIPTION OF THE DRAWINGS

FIG. 1 is a cross section of a desorption apparatus containing four hard rollers which are coated with the sorbent material and opposed plates as electrodes.

FIG. 2 is a side view of the apparatus of FIG. 1 with a portion of the outer shell removed to show the alignment of the rollers.

FIG. 3 is a cross section of an apparatus containing six soft rollers which are either constructed of a sorbent material or are coated with such a material and a cylindrical outer electrode.

FIG. 4 illustrates the arrangement of a multiplicity of electrophoretic moving boundary separators in use in network.

DESCRIPTION OF THE PREFERRED EMBODIMENT

As stated above, the process of the present invention provides a continuous method for separating components of a fluid mixture. The invention requires that separate chambers be connected by a rotatable sorbent barrier which will continuously alternate the sorbent face exposed to each chamber and that an electrical potential be imposed to promote sorption and/or desorption. The rotation rate and/or the electrical field intensity can be varied to optimize separation in conjunction with the fluid stream throughput and the sorption/desorption conditions.

As stated above, a fluid mixture is caused to flow into the sorption zone wherein the conditions are such to promote sorption of one of the components of the mixture by the sorbent material. Then conditions are created in the desorption zone to promote the desorbing of the sorbed component when the sorbent material containing it moves into the desorption zone. Such "conditions" will include the imposition of an electrical potential in either the sorption or desorption zone or in both. Thermodynamic variables such as temperature and pressure can be used to influence the sorption or desorption of the component of the original fluid mixture. Other variables such as pH, concentration of other chemical species, or changed tension on an elastomeric sorbent surface can also be used to influence the sorption/desorption process. Examples of fluid separations which can be performed according to the method of the present invention are human hemoglobin and human serum albumin or protein mixtures generally.

Electrophoresis is a process whereby substances absorbed on a gel or other solid through which they can diffuse are allowed to do so when the solid is subjected to an electrical field. Sorbate migration is toward electrodes of charge opposite to that of the charged substances. The migrated particles lose their charge at the electrode and generally agglomerate around it. In the present application, the phenomena of electrophoresis is utilized to cause migration of charged particles into and out of a sorbent material.

The process of the present invention can also be used to mix fluid components together. Mixing is accomplished in exactly the same manner as separation--the difference is only in which side of the process, sorption or desorption, is considered the product stream. The mixing mode is useful in preparing fluid mixtures of precise composition where the metered component is carried into the desorption or product chamber by the sorbent material. The product chamber might in fact be a reaction chamber where the feed of the sorbent-carried reactant is rate controlling. An example of this is a process in which amino acids or amino acid organic base compounds with net acidic character are desorbed into a solution of organic base.

The present invention is using the phenomenon of electrophoresis on the moving boundary sorbent barrier described above. An electrical potential is used to encourage or drive certain charged particles either to or away from the surface containing the sorbent material and thus it encourages the sorption of such charged components by the sorbent material or, in the desorption zone, encourages the desorption of the charged particles from the sorbent material. The electrical field is used to provide selective absorption by enhancing sorption of one or a few of the components of the mixture. For example, if several components of a mixture may be absorbed by sorbent material but one of them is a charged particle, its sorption can be enhanced up by imposition of an electrical field of appropriate charge distribution.

This electrophoretic technique has many advantages but probably the greatest advantage is its flexibility since two rate controlling parameters are easily varied. The first is the electrical field strength and the second is the rotation rate of the moving boundary. Also, the thermodynamic conditions in the sorption and desorption zones can be altered. One advantage of being able to vary the field strength is that with complete recycle of a batch sample, an analysis can be performed as compounds are separated based on their permeability while the field strength is gradually increased. The rotation rate could be decreased over time to compensate for the decreasing concentration.

It is possible to impose different electric fields in different directions to prevent components with charge like that at the outlet from flowing axially out of the separator. The purpose of this would be to maintain it within the separator so that it can be more completely separated sorptively in one pass. This is particularly applicable to the embodiment of the present invention wherein separate separators are used in series to separate different components of a mixture.

Blocking elements or masks can be used in the sorption zone to influence the selectivity of the sorption by changing the available surface area for sorption. With the electrophoretic technique, the blocking elements or masks can be used to cause the desorption to take place in a specific place within the desorption zone because the sorbed component will keep migrating inwards reducing the sorbate concentration at the surface as the blocking element is passed. This will create a low mass transfer region both at the location of the mask and immediately following it in the desorption zone.

It is possible to create a desired electrical field with only one electrode but it is preferable to use at least two electrodes, one positive and one negative, to provide both pushing and pulling forces. In some circumstances, this can increase the efficiency of the separator.

For the purposes of this invention sorbent materials are generally of four types:

1. Solids which can absorb gases in the bulk of the material. For example FeTi, LaNi$_5$, and the other so-called metal hydrides can absorb hydrogen. Solids with a high specific surface such as Fuller's earths, bauxite, alumina, gas adsorbent carbon, silica gel and zeolites (aluminosilicates) can be used. In some of these latter examples considerable temperature elevation is required to regenerate the adsorptivity. This might necessitate some modification of the apparatus design so that the desorption chambers can withstand the heat.

2. Porous insoluble solids containing absorbent liquids, such as carboxy-methyl cellulose, (CMC)/water, or saponified starch-g-polyacrylonitrile, (HSPAN)/water, can be used. In either case the water is strongly bound to the solid but is still as absorptive as pure water. Other polar solvents or aqueous solutions could be used with these solids (CMC or HSPAN) but it is likely that modification of the constituent solid would be the preferred way to optimize a particular gas absorption application. Generally, the polarity of the solid should match that of the chosen absorbent liquid to maximize liquid content in the sorbent combination. Consequently, various hydrocarbon-swellable polyolefins would provide suitable mechanical support for alkanes or other nonpolar liquids.

3. Gels formed from solvents and soluble solids such as polymers of soluble monomers can also be used. The distinction from (2) is that in this case the solid does not provide any structural form and therefore the gel can be applied as a coating to an existing solid or possibly cast into appropriate form. Examples are protein/water, cellulose acetate/water, ABS polymers/ketones, and polystyrene/aromatic solvents.

4. Solids formed from a combination of fluids that solidify under conditions in the sorption chamber, especially where one of the fluids is the sorbed component, can be used. This is the most complicated case from the standpoint of designing a process in which the sorption phase seals the chambers. However, it is the only one where elasticity of the sorbent will not be necessary to achieve a tight fit between the moving elements. Examples would be hydrate formation or reversible polymerization of a fluid monomer being removed from a mixture with nonpolymerization components. It is possible that if one of the combining components is more or less permanently fixed to the moving element, e.g. water in the case of hydrate formulation, it could be supported in or with a solid material such as cases (2) and (3) above.

It is very important to the present invention that the sorbent material provides the seal which separates the sorption zone from the desorption zone. In order to accomplish this, the sorbent material may be deformable so that it can provide an acceptable seal. The separation between the sorption and desorption zones can be provided by a combination of one or more rollers, and one or more moving belts and also by the combination of two or more moving belts without any rollers. In the first case, either the rollers (or the belts, or both) may have the sorbent material at least one the surfaces thereof (and in the latter case, one, part, or all of the belts may have the sorbent material thereon). In fact, it is possible to use more than one type of sorbent so that more than one selectivity for the sorbed component is possible with the apparatus of this invention. An important aspect of all of the embodiments of this invention is that the rollers (or belts) be in engagement so that the sorbent material forms a boundary between the sorption and desorption zones.

FIG. 1 illustrates one particular embodiment of the present invention which is comprised of a housing 10 which has four inflexible rotating rollers 12 disposed therewithin. The rollers 12 are in series engagement with each other forming a polygonal cylinder. The rollers 12 and the housing 10 thus form a sorption zone B at the center of the rollers 12 and four separate desorption zones A between the rollers 12 and the inside wall of the housing 10. The rotation of the rollers is indicated by the arrows. The rollers are coated with a sorbent material which provides the seal between the sorption and desorption zones. In order to protect the seal between the zones, deformable sealing rollers 24 are provided at the nip of each pair of rollers 12 and also at each nip of the rollers 12 and the inside wall of the housing 10.

Feed fluid enters the apparatus through the sorption zone inlet 16 where it comes into contact with the sorbent material. Inlet 16 is also a charged electrode. Charged plates 28 are oppositely charged. At least one of the charged components of the feed fluid is absorbed by the sorbent material in the sorption zone B and then desorbed in desorption zone A after the roller 12 containing sorbent material rotates into desorption zone A. The sorbed component leaves desorption zone A through the desorption zone ports 26 which are connected to the desorption manifold 20 and then flow out of the desorption zone outlet 22. The fluid from which the component was absorbed flows out of the sorption zone outlet 18.

FIG. 3 illustrates another embodiment of the present invention wherein six flexible rotating rollers 12 are disposed within a housing 10 which is a charged electrode. The rollers 12 are either formed of a flexible absorbent material or are coated therewith. Again, the sorbent material provides the seal between sorption zone B and desorption zone A. The feed gas enters the sorption zone inlet 16, which is also a charged electrode, and the desorbed components exit the apparatus through the desorption zone outlet 22.

The electrophoretic moving boundary separators may be connected in a network according to the present invention so that different components of a fluid mixture can be selectively absorbed in each of the separators. The network can be a linear series as shown in FIG. 4. This process performs a similar function as that performed in a continuous chromatograph but does not require cyclic operation to produce the continuous effect. The conditions in each of the separators, i.e. electrical field, rate of rotation, temperature, pressure, flow rate, pH, sorbent, etc., can be adjusted independently for the sorption of different components of a fluid mixture or for optimal separation of progressively lower concentrations of the same sorbed material.

FIG. 4 illustrates how three electrophoretic moving boundary separators 50, 52 and 54 are used in series for the separation of fluid mixtures. The separators may be constructed as shown in FIGS. 1 or 2. In one use of the process of the present invention, a fluid mixture to be treated enters separator 50 through feed line 46 and the component to be separated leaves through line 48. If it is desired to use a carrier fluid in the desorption of any of the separators, then such carrier will enter through carrier feed line 30. The rest of the feed fluid mixture exits the separator 50 through line 32 and is conveyed to separator 52.

Separator 52 may utilize a different sorbent or may have different operating conditions and varying electric field as mentioned above. Its purpose may be to separate the same component that was separated in separator 50 or its purpose may be to separate a different component of the original fluid mixture. The desorption product leaves through line 34. If a carrier fluid is necesary, then it will enter through line 36. The remainder of the fluid mixture leaves separator 52 through line 38 and is conveyed to separator 54 wherein a further separation takes place and the desorption product leaves through line 40. Optional carrier fluid will enter through line 42. What is left of the fluid mixtures leaves separator 54 through line 44.

The fact that the separator elements can be held at a steady sorption condition allows them to be deliberately adjusted and thus act as analytical instruments. Sorption-type analytical separations are conventionally carried out by chromatography or sometimes with a series of filters. My invention has a potential advantage over these "linear" methods in that a branched separation scheme can be constructed with flow switches and sorption parameters in the network controlled manually or automatically using information from on-line sensors. The sorption character of the early (initially encountered) moving boundary separators would be of a general nature and the composition could be 'scanned' by having a parameter, such as sorption temperature for example, automatically increase or decrease until a product (or products) is sensed in this stream, a valve would direct it to another separator whose sorption parameters would be adjusted based on the information generated by the preceding sensors. The stream carrying the originally unsorbed components would be sent to a separator whose sorption parameters could likewise be controlled.

A machine based on such a scheme would be particularly useful for separation of complex mixtures containing a large number of species such as biological mixtures. Parameter and switch control could be carried out by computer. It would be desirable to have a diluent fluid that could be cleanly separated from or added to the mixture. Water would be an obvious diluent for many aqueous solutions. Since the mixture components fed are not consumed by the sorption process, if nondegradative-type sensing such as spectrophotometry is used, all product streams could be returned to the feed supply vessel to reconstitute the feed. Thus with appropriate diluent addition and/or removal as needed to fill the separators and interconnecting lines, the reconstituted sample could be reseparated with different initial sorption conditions and the original analysis confirmed or not. The retesting capability would be especially advantageous when calibrating the machine with known compounds and mixtures since the sorption dependence on conditions could be determined and logged into the computer memory in a straightforward manner.

A machine to produce purified pharmaceuticals or fine chemicals could be designed after the sorption network described above. It would have advantage of being readily adjusted to produce various chemicals so that the process streams might change weekly or daily without machine alterations other than sorption conditions in the separators and flow control changes. To produce a pure stream output the sorbent boundary rotation rate and sorption conditions would be adjusted to give the sharpest separation of the desired component in the pure product stream and the other stream would be partly recycled to the optimized separator, as necessary to increase yield of the desired product. This product stream could in turn be directed to a second separator and the stream refined further in the same manner and so on to a limit set by the amount of the desired component left to purify.

Finally, a reactive system could be organized using a similar sorption network scheme. In this case the sorption process would involve sorption/reaction on the moving boundary, for example, a surface containing immobilized enzymes, with products being desorbed and either separated in a downstream sorption separator or reacted further in following sorption reactors. The system would not be limited to the use of sorption separator elements. If appropriate, conventional process elements such as membrane separation, dialysis or precipitation units, could be included in the overall process.

Reactive processes on use of immobilized cells or even enzyme mixes are especially dependent on rapid and efficient removal of biological and particularly cellular products because of the presence of overproduct inhibitory processes which cut off further reaction and either destroy the desired product or create undesired byproducts at a certain level of product in the environment. The sorptivity of the separator element can be viewed as a simple analog to the permeability of the cell membrane. The sorption separator selectively transports compounds with an affinity to the sorbent to a new environment, disengages them and returns to the sorption zone. In a cell, this function is performed by extremely specific molecules embedded in the cell wall.

I claim:

1. A continuous process for separating charged components of a fluid mixture which comprises:
   (a) forming a sorption zone and desorption zone, said zones being separated by a boundary of a sorbent material which is disposed on the outside of a plurality of rotating elements and which continuously moves back and forth between the zones, said boundary forming a seal between the zones, and said sorbent material or support for the sorbent material being deformable to provide an acceptable seal,
   (b) causing a fluid mixture containing charged components to be separated to flow into the sorption zone,
   (c) imposing an electrical potential in the sorption zone to promote preferential sorption of at least one of the charged components by the sorbent material, and
   (d) imposing an electrical potential in the desorption zone to promote desorption of at least one of the sorbed components when the sorbent material containing the sorbed components moves into the desorption zone.

2. The process of claim 1 wherein there is disposed between the two zones, a number of rotating rollers which have the sorbent material at least on the surface thereof and which are in engagement in series.

3. The process of claim 1 wherein the desorbed component forms a part of a second fluid mixture which is present in the desorption zone.

4. The process of claim 3 wherein the desorption zone is a reaction zone and the rate of reaction is controlled by the amount of desorbed component which enters the desorption zone.

5. The process of claim 1 wherein:
   (e) the product of at least one of said zone is conveyed to another separator where steps (a), (b), (c) and (d) are repeated, and
   (f) step (e) is repeated as many times as desired.

6. A continuous process for separating charged components of a fluid mixture which comprises:
   (a) forming a sorption zone and desorption zone, said zones being separated by a boundary of a sorbent material which is disposed on the outside of a plurality of rotating elements and which continuously moves back and forth between the zones, said boundary forming a seal between the zones, and said sorbent materail or support for the sorbent material being deformable to provide an acceptable seal,
   (b) causing a fluid mixture containing charged components to be separated to flow into the sorption zone,
   (c) imposing an electrical potential in the sorption zone to promote preferential sorption of at least one of the charged components by the sorbent material, and
   (d) creating conditions in the desorption zone to promote desorption of at least one of the sorbed components when the sorbent material containing the sorbed components moves into the desorption zone.

7. The process of claim 6 wherein there is disposed between the two zones, a number of rotating rollers which have the sorbent material at least on the surface thereof and which are in engagement in series.

8. The process of claim 6 wherein the desorbed component forms a part of a second fluid mixture which is present in the desorption zone.

9. The process of claim 8 wherein the desorption zone is a reaction zone and the rate of reaction is controlled by the amount of desorbed component which enters the desorption zone.

10. The process of claim 6 wherein:
    (e) the product of at least one of said zones is conveyed to another separator where steps (a), (b), (c) and (d) are repeated, and
    (f) step (e) is repeated as many times as desired.

11. A continuous process for separating charged components of a fluid mixture which comprises:
    (a) forming a sorption zone and a desorption zone, said zones being separated by a boundary of a sorbent material which is disposed on the outside of a plurality of rotating elements and which continuously moves back and forth between the zones, said boundary forming a seal between the zones, and said sorbent material or support for the sorbent material being deformable to provide an acceptable seal, (b) causing a fluid mixture containing charged components to be separated to flow into the sorption zone, (c) creating conditions in the sorption zone to promote sorption of at least one of the charged components by the sorbent material, and (d) imposing an electrical potential in the desorption zone to promote desorption of at least one of the sorbed components when the sorbent material containing the sorbed components moves into the desorption zone.

12. The process of claim 11 wherein there is disposed between the two zones, a number of rotating rollers which have the sorbent material at least on the surface thereof and which are in engagement in series.

13. The process of claim 11 wherein the desorbed component forms a part of a second fluid mixture which is present in the desorption zone.

14. The process of claim 13 wherein the desorption zone is a reaction zone and the rate of reaction is controlled by the amount of desorbed component which enters the desorption zone.

15. The process of claim 11 wherein:

(e) the product of at least one of said zones is conveyed to another separator where steps (a), (b), (c) and (d) are repeated, and (f) step (e) is repeated as many times as desired.

* * * * *